(12) United States Patent
Fortier

(10) Patent No.: US 9,474,531 B2
(45) Date of Patent: Oct. 25, 2016

(54) LIGATING BAND DISPENSER WITH TRANSVERSE RIDGE PROFILE

(75) Inventor: Richard Fortier, Concord, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2362 days.

(21) Appl. No.: 11/345,336

(22) Filed: Feb. 2, 2006

(65) Prior Publication Data

US 2006/0129167 A1    Jun. 15, 2006

Related U.S. Application Data

(63) Continuation of application No. 10/166,115, filed on Jun. 11, 2002, now Pat. No. 7,063,709.

(51) Int. Cl.
*A61B 17/12* (2006.01)
*A61B 17/00* (2006.01)

(52) U.S. Cl.
CPC ........... *A61B 17/12013* (2013.01); *A61B 2017/00296* (2013.01); *A61B 2017/00907* (2013.01); *A61B 2017/12018* (2013.01)

(58) Field of Classification Search
CPC ............... A61B 17/12013; A61B 2017/12018
USPC ........ 606/139, 140; 227/345, 434, 447, 466, 227/602, 604, 910
See application file for complete search history.

(56) References Cited

U.S. PATENT DOCUMENTS

| | | | |
|---|---|---|---|
| 1,822,194 A * | 9/1931 | Fichthorn et al. | ............... 57/77 |
| 4,938,765 A | 7/1990 | Rasmusson | |
| 5,269,789 A * | 12/1993 | Chin et al. | ................... 606/140 |
| 5,320,630 A * | 6/1994 | Ahmed | ........................ 606/140 |
| 5,356,416 A * | 10/1994 | Chu et al. | ..................... 606/140 |
| 5,398,844 A | 3/1995 | Zaslavsky et al. | |
| 5,423,834 A | 6/1995 | Ahmed | |

(Continued)

FOREIGN PATENT DOCUMENTS

| EP | 0 679 368 | 11/1995 |
|---|---|---|
| EP | 1 145 684 | 10/2001 |

(Continued)

OTHER PUBLICATIONS

Nobuatsu Koyama et al., Endoscopic Resection Using a Ligating Device for Esophageal Granular Cell Tumors: A Report of Two Cases. Digestive Endoscopy, vol. 12, Issue 3, pp. 240-242 (Jul. 2000).

*Primary Examiner* — Sarah W Aleman
(74) *Attorney, Agent, or Firm* — Fay Kaplun & Marcin, LLP

(57) ABSTRACT

An improved distal end for a ligating band dispenser having a transverse groove or ridge profile that promotes rolling of the bands. In one embodiment, the ligating bands and the transverse grooves or ridges are dimensioned such that the width of the bands when stretched on the support surface is substantially the same as the pitch of the transverse grooves or ridges. Having the width of the bands when stretched on the support surface be substantially the same as or less than the pitch of the transverse grooves or ridges allows the bands to fit within the grooves, which helps insure that the bands are sufficiently held back by the ridge crests to induce a rolling action. In addition, the transverse grooves or ridges may also be dimensioned such that the height of the ridge crests is sufficiently high to insure that the bands are sufficiently held back by the ridge crests to induce a rolling action.

11 Claims, 5 Drawing Sheets

(56) References Cited

U.S. PATENT DOCUMENTS

| | | | |
|---|---|---|---|
| 5,462,559 A | 10/1995 | Ahmed | |
| 5,507,797 A | 4/1996 | Suzuki et al. | |
| 5,569,268 A * | 10/1996 | Hosoda | 606/140 |
| 5,624,453 A * | 4/1997 | Ahmed | 606/140 |
| 5,853,416 A | 12/1998 | Tolkoff | |
| 5,857,585 A * | 1/1999 | Tolkoff et al. | 221/36 |
| 5,913,865 A * | 6/1999 | Fortier et al. | 606/140 |
| 5,968,056 A | 10/1999 | Chu et al. | |
| 6,059,798 A * | 5/2000 | Tolkoff | 606/140 |
| 6,099,535 A | 8/2000 | Lamport et al. | |

FOREIGN PATENT DOCUMENTS

| | | |
|---|---|---|
| EP | 1 147 744 | 10/2001 |
| WO | WO 97/45060 | 12/1997 |

* cited by examiner

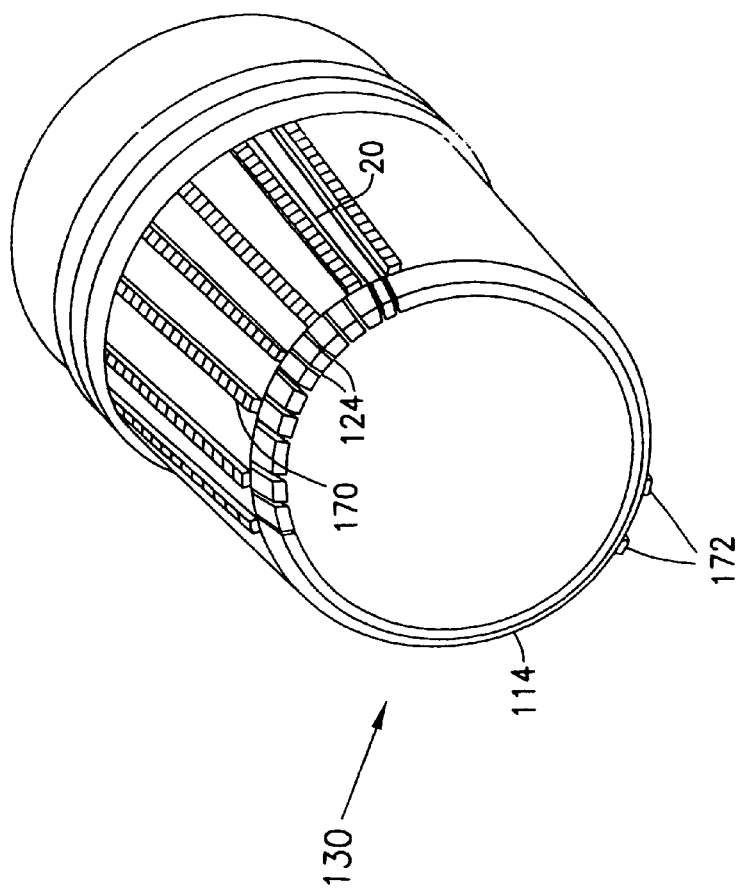
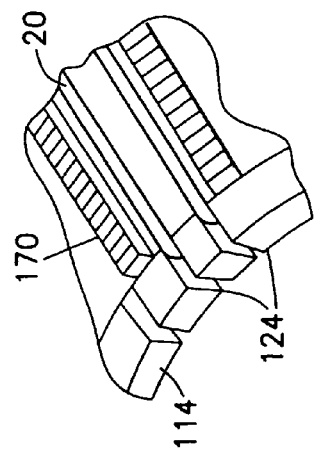
Fig. 3
PRIOR ART
Fig. 4
PRIOR ART

LIGATING BAND DISPENSER WITH TRANSVERSE RIDGE PROFILE

RELATED APPLICATIONS

This application is a continuation of U.S. application Ser. No. 10/166,115, filed Jun. 11, 2002 now U.S. Pat. No. 7,063,709, which is incorporated herein in its entirety by reference thereto.

FIELD OF THE INVENTION

The present invention relates generally to the field of tissue ligation, and more particularly to an improved distal end for a device for dispensing ligating bands.

BACKGROUND INFORMATION

Physicians have used elastic ligating bands to treat lesions, including internal hemorrhoids and mucositis and for performing mechanical hemostasis. The object of such ligation is to position a ligating band, which is usually elastic, over the targeted lesion or blood vessel section by first stretching the band beyond its undeformed diameter and then drawing the tissue to be ligated within the band. Thereafter the band is released so that it contracts, applying inward pressure on the section of tissue caught within the band. The effect of the inward pressure applied by the band is to stop all circulation through the targeted tissue, thereby causing the tissue to die. The body then sloughs off the dead tissue, or the dead tissue may be aspirated into an endoscope or a similar device.

Some previous ligating band dispensers allowed a user to dispense only a single ligating band at a time. That is, after a single ligating band was dispensed, if a user wanted to ligate another portion of tissue, the user would remove the device from the patient's body, load a new ligating band on the device and reinsert the device to the desired area within the patient's body.

U.S. Pat. No. 5,398,844 to Zaslavsky et al. ("the Zaslavsky '844 patent"), which is expressly incorporated by reference herein, describes a ligating band dispensing device including a substantially cylindrical support surface over which elastic ligating bands are stretched. The cylindrical support surface is typically attached to the distal end of an endoscope which is advanced into the body to a target area. A user then applies suction through the endoscope to draw the tissue to be ligated into the cylindrical support surface and releases a ligating band to contract around the tissue. While the device of the Zaslavsky '844 patent allows a user to place several ligating bands at desired locations without removing the device from the patient's body to reload ligating bands, it requires multiple pull strings to deploy the ligating bands. These pull strings may interfere with each other, may become tangled, or may take up excessive room in the endoscope working channel, thereby preventing the use of catheter-type accessory devices. In addition, as the number of ligating bands included on the distal end of these devices is increased, the number of pull strings increases while the dispenser itself elongates. Accordingly, the field of vision from the endoscopes to which these devices are normally coupled has been correspondingly decreased.

U.S. Pat. No. 5,853,416 to Tolkoff ("the Tolkoff '416 patent") and U.S. Pat. No. 6,059,798 ("the Tolkoff '798 patent"), both of which are expressly incorporated by reference herein, describe a distal end for a ligating band dispenser wherein a plurality of ligating bands can be actuated sequentially by the same trigger line. In addition, the bands can be located at a certain distance away from the distal end of the device, and all or part of the cylindrical support surface may be transparent for visualization.

U.S. Pat. No. 5,913,865 to Fortier et al. ("the Fortier '865 patent"), which is also expressly incorporated by reference herein, also describes a distal end for a ligating band dispenser that also allows a plurality of ligating bands to be actuated sequentially by the same trigger line. The supporting structure as shown in the embodiment of FIGS. 5-14 of the Fortier '865 patent includes a plurality of slots in the distal end of the device that are arranged so that the trigger line need only pass through each slot once. This helps prevent neighboring passes of the trigger line from becoming twisted or tangled with one another. In addition, the Fortier '865 patent describes that the slots can have alternating depths, such that alternating shallow slots and deeper slots are disposed on the distal end for retaining the trigger line. With such an arrangement, the lead part of the trigger line may be positioned in the shallower of two neighboring slots, thus insuring that the lead part of the trigger line is closer to the distal rim of the device. This increases deployment reliability. The deeper slot helps prevent the trigger line from coming off prematurely. In addition, each of the slots may be narrower than the trigger line, which also helps prevent the trigger line from prematurely exiting the slots.

As described in the Fortier '865 patent, and as shown in the embodiment of FIGS. 17-19 of that patent, the support surface also may include a plurality of axially extending ridges to assist in the deployment of the ligating bands by preventing the bands from sliding along the trigger line and facilitating rolling of the bands along the support surface. Having the bands roll, instead of slide, along the support surface promotes deployment of the bands. If a band slides along the support surface, it may not deploy. The axially extending ridges are described as having a frictional surface, which may include, for example, a plurality of transverse grooves or a sawtooth profile. (Col. 8, lines 2-4).

While the entire disclosure of the Fortier '865 patent is expressly incorporated by reference herein, specific reference is made to the embodiment of FIGS. 5-14 and the embodiment of FIGS. 17-19, as discussed above. Like the rest of the Fortier '865 patent, the description and illustration of these embodiments, including the means for deployment of the bands, is expressly incorporated herein by reference.

Physicians, when using a device such as one of the above-mentioned devices, often apply a lubricant to the device, to aid in intubation. While the lubricant aids in intubation, it also reduces the friction between the ligating bands and the support surface. The reduced friction may cause the ligating bands to slide instead of roll along the support surface, and hence may reduce the probability of a successful band deployment.

SUMMARY OF THE INVENTION

The present invention is directed toward providing an improved distal end for a ligating band dispenser, wherein the device has an improved transverse groove or ridge profile that promotes rolling of the bands instead of sliding.

In one embodiment, the ligating bands and the transverse grooves or ridges on the support surface are dimensioned such that the width of the bands when stretched on the support surface is substantially the same as the pitch of the transverse grooves or ridges on the support surface. In another embodiment, the ligating bands and the transverse grooves or ridges on the support surface are dimensioned such that the width of the bands when stretched on the support surface is less than the pitch of the transverse grooves or ridges on the support surface. Having the width of the bands when stretched on the support surface be substantially the same as or less than the pitch of the transverse grooves or ridges on the support surface allows the bands to fit within the grooves. This helps insure that the bands are sufficiently held back by the ridge crests to induce a rolling action.

In another aspect of the invention, in addition to having the pitch of the transverse grooves or ridges be substantially the same as or greater than the width of the stretched bands, the transverse grooves or ridges may also be dimensioned such that the height of the ridge crests is sufficiently high to insure that the bands are sufficiently held back by the ridge crests to induce a rolling action.

BRIEF DESCRIPTION OF THE DRAWINGS

The present invention will be more readily understood through the following detailed description, with reference to the accompanying drawings, in which:

FIG. 3 is a perspective view of a prior art ligating dispenser device;

FIG. 4 is a perspective view of a portion of the prior art ligating dispenser device of FIG. 3;

DETAILED DESCRIPTION OF THE INVENTION

Figure 2:
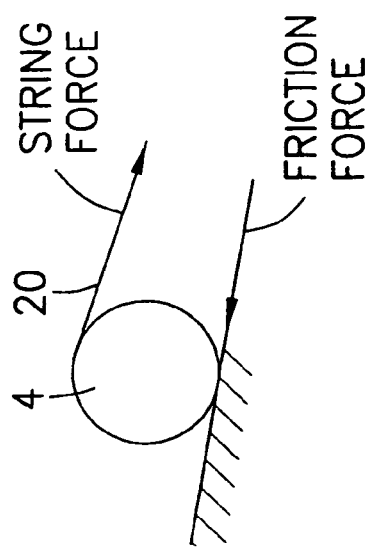
FIG. 2 is an expanded view of a highlighted portion of FIG. 1.
Figure 1:
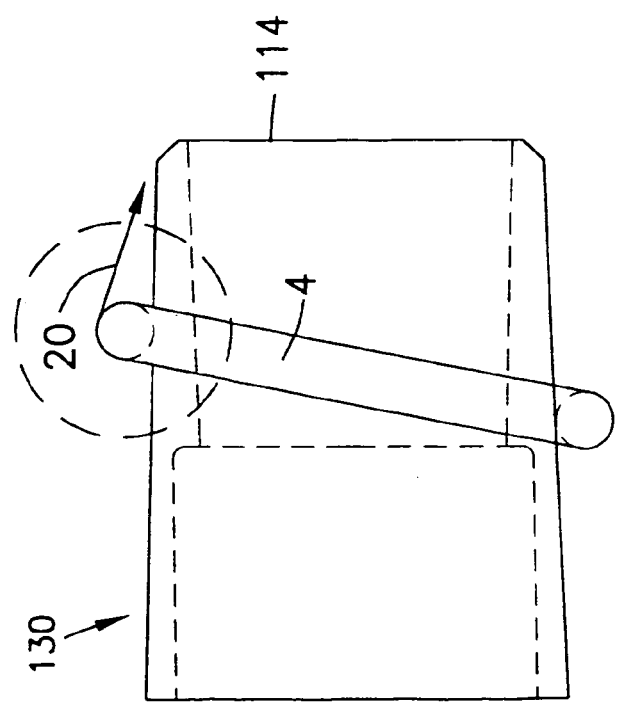
FIG. 1 is a side view of a prior art ligating dispenser device illustrating the forces affecting movement of a ligating band.

FIGS. 1 and 2 illustrate the forces involved in the deployment of a ligating band 4, FIG. 2 being an expanded view of the highlighted portion of FIG. 1. In any design in which the bands 4 are pulled towards the distal end 114 of a support surface 130, reliable band deployment is facilitated by the bands rolling rather than sliding across the support surface 130. The rolling action is caused, for example, by the trigger line 20 pulling over the top of the band 4 and by friction between the band 4 and the support surface 130. Rolling is initiated, for example, at the point in which the trigger line 20 contacts the band 4, and propagates around the band circumference. This rolling causes the band 4 to move distally.

Potential problems are created when the band 4 slides instead of rolls. If the band 4 slides across the support surface 130, that portion of the band 4 at the trigger line 20 may reach the distal rim of the support surface, thereby allowing the trigger line 20 to come free from one or more slots 124 in the distal rim (slots 124 are shown in FIG. 3), prior to motion being initiated in the band 4 at a position diametrically opposite the trigger line 20. This leaves the band 4 with no effective trigger line 20. Also, if the band 4 slides across the support surface 130, it tends to push the trigger line 20 ahead of it. This too may cause the trigger line 20 to come out of the slots, leaving the band 4 with no effective trigger line 20. The trigger line 20 itself often exacerbates this problem, because it provides the bands 4 with a relatively low-friction surface, increasing the chance of sliding. Also, with sliding motion, there is less of a tendency for the band 4 to move at the point of the support surface 130 opposite the trigger line 20. This is particularly true if the bands 4 undergo heating from, for example, a typical sterilization cycle.

Figure 5:
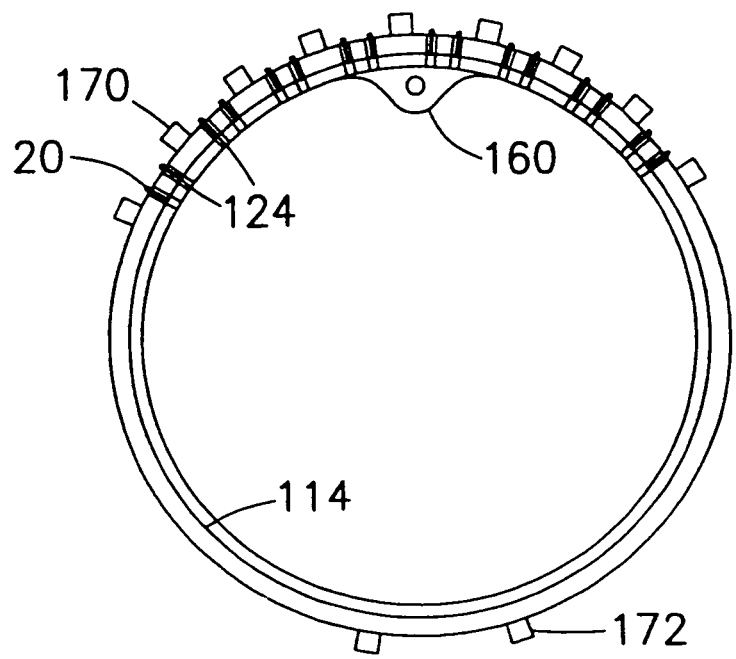
FIG. 5 is a front view of the prior art ligating dispenser device of FIG. 3.

As shown in FIG. 3, an example of a prior art support surface 130 includes, for example, a plurality of primary ridges 170 and at least one secondary ridge 172 to facilitate rolling of the bands 4. As shown in FIGS. 3-5, the primary ridges 170 may be disposed in the vicinity of the slots 124. In an exemplary arrangement, the primary ridges 170 may be arranged so that a pair of slots 124 are disposed between each adjacent pair of primary ridges 170. If the support surface 130 also includes alternating shallow slots and deeper slots, then one of each type of slot may be disposed, for example, between each corresponding pair of primary ridges 170. Alternatively, all of the slots 124 may have the same depth. As described in U.S. Pat. No. 5,913,865, a ring 160 may serve as a guide for trigger line 20.

The primary ridges 170 are preferably thick enough so that the bands 4 are maintained remote of the trigger line 20. In this manner, bands 4 are unable to slide along or push trigger line 20.

The support surface 130 in FIGS. 3-5 also includes, for example, at least one axially extending secondary ridge 172. A pair of secondary ridges 172 are shown. Secondary ridges 172 reduce, for example, the contact area between the bands 4 and the support surface 130, thereby reducing the tendency of the bands 4 to stick to the support surface 130. In addition, secondary ridges 172 also allow lubricant, which is often applied to the support surface 130 to aid insertion into the patient, under the bands 4, further assisting propagation. The secondary ridges 172 are preferably disposed, for example, substantially diametrically opposite any primary ridges 170 (if present), meaning simply that the secondary ridges 172 are preferable disposed, in relation to the primary ridges 170, on the opposite side of the circumference of the support surface 130. This configuration is illustrated in FIGS. 3 and 5. The primary ridges 170 and secondary ridges 172 could alternatively be formed around the entire circumference of the support surface 130, essentially forming a series of ridges that span the circumference of the support surface 130.

Figure 7:
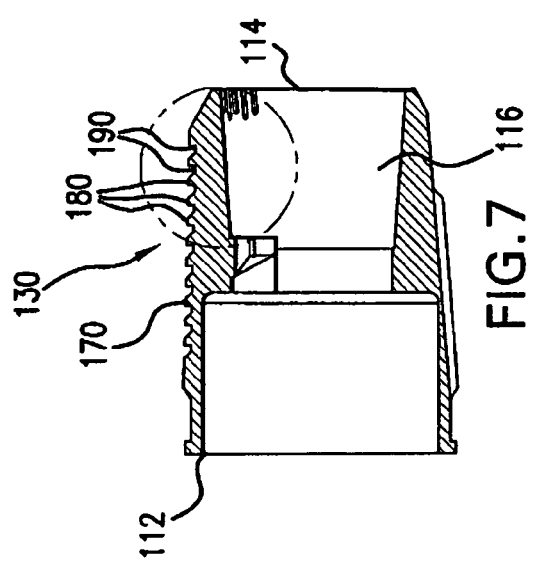
FIG. 7 is a cross-sectional view of a distal end of a ligating band dispenser device.

FIG. 7 is a cross-sectional view of a distal end of a ligating band dispensing device. The ligating band dispensing device comprises a supporting structure comprising a substantially cylindrical support surface 130 adapted to receive a plurality of ligating bands and a trigger line on an outer surface. The support surface 130 has a proximal end 112 and a distal end 114 and a channel 116 extending axially therethrough. The support surface 130 includes at least one axially extending primary ridge 170 disposed on the outer surface. The primary ridge 170 includes a plurality of transverse ridges 180 on its outer face. The transverse ridges 180 form transverse grooves 190 between the transverse ridges 180.

Some examples of dimensions for the device are as follows. The support surface may have, for example, a length of approximately 0.6 to 0.8 inches and an outer diameter of approximately 0.4 to 0.6 inches. The channel may have a diameter of approximately 0.3 to 0.55 inches. The slots may have a depth of approximately 0.01 to 0.04 inches and a width of approximately 0.006 to 0.01 inches. If slots of alternating depths are used, the shallow slots may have a depth of approximately 0.01 to 0.02 inches, and the deeper slots may have a depth of approximately 0.02 to 0.04 inches, each with a width of approximately 0.006 to 0.01 inches. The slots may be arranged around the distal end with an angular spacing of approximately 6 to 10 degrees between adjacent slots.

The Fortier '865 patent describes that the primary ridges 170 may include a frictional surface on their outer face (the face contacting the bands 4). The frictional surface may include, for example, a plurality or transverse grooves or a sawtooth profile. The frictional surface increases the tendency of the bands 4 to roll rather than slide, increasing deployment reliability. The Fortier '865 patent, however, provides no description of the size, spacing or number of grooves.

Figure 6:
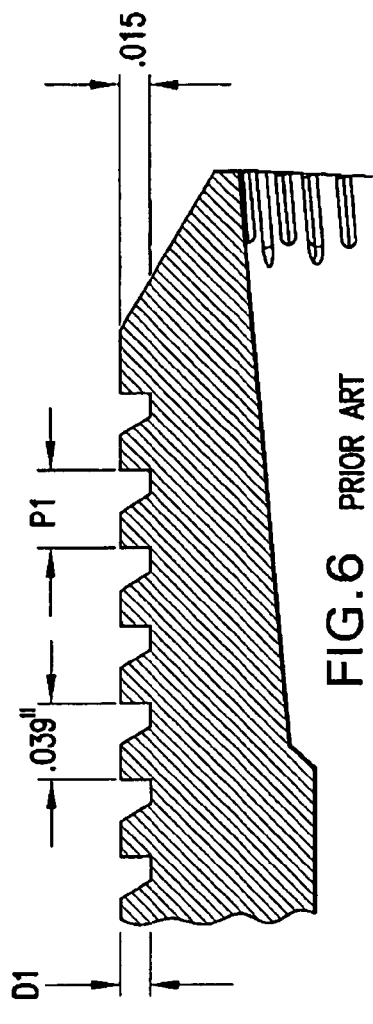
FIG. 6 is an enlarged view of a portion of a ridge profile of a prior art ligating dispenser device.

FIG. 6 shows the groove profile of the first commercial embodiment of the Fortier '865 patent having transverse grooves, the prior art SPEEDBAND™ SUPERVIEW ligating device (Boston Scientific Corp.). As shown in FIG. 6, that device had a groove pitch P1 of approximately 0.039" and groove depth D1 of approximately 0.015". This device was used with ligating bands that had a relaxed (off housing) outer diameter (OD) of 0.229", a relaxed inner diameter (ID) of 0.075", a relaxed wall height (i.e., the distance between the ID and OD) of 0.077", and a relaxed width (measured in the direction along an axis passing through the center of the band) of 0.077". Because the width was substantially the same as the wall height, the cross-section geometry of these bands was substantially square. When stretched onto the housing as shown in FIG. 6, the width of the bands was reduced to approximately 0.050". Since the groove pitch was approximately 0.039", the width of the bands was thus approximately 28% greater than the groove pitch, making the width of the bands substantially greater than the groove pitch.

FIG. 7 is a cross-sectional view of a distal end of a ligating band dispensing device. The ligating band dispensing device comprises a supporting structure comprising a substantially cylindrical support surface 130 adapted to receive a plurality of ligating bands and a trigger line on an outer surface. The support surface 130 has a proximal end 112 and a distal end 114 and a channel 116 extending axially therethrough. The support surface 130 includes at least one axially extending primary ridge 170 disposed on the outer surface. The primary ridge 170 includes a plurality of transverse ridges 180 on its outer face. The transverse ridges 180 form transverse grooves 190 between the transverse ridges 180.

In another version of the prior art SPEEDBAND™ SUPERVIEW ligating device (Boston Scientific Corp.) using the housing as shown in FIG. 6, ligating bands were used having a relaxed (off housing) outer diameter (OD) of 0.259", a relaxed inner diameter (ID) of 0.075", a relaxed wall height (i.e., the distance between the ID and OD) of 0.092", and a relaxed width (measured in the direction along an axis passing through the center of the band) of 0.077". Because the width was smaller than the wall height, the cross-section geometry of these bands was substantially rectangular. When stretched onto the housing as shown in FIG. 6, the width was again reduced to approximately 0.050". Again, since the groove pitch was approximately 0.039", the width of the bands was approximately 28% greater than the groove pitch, making the width of the bands substantially greater than the groove pitch.

Figure 8:
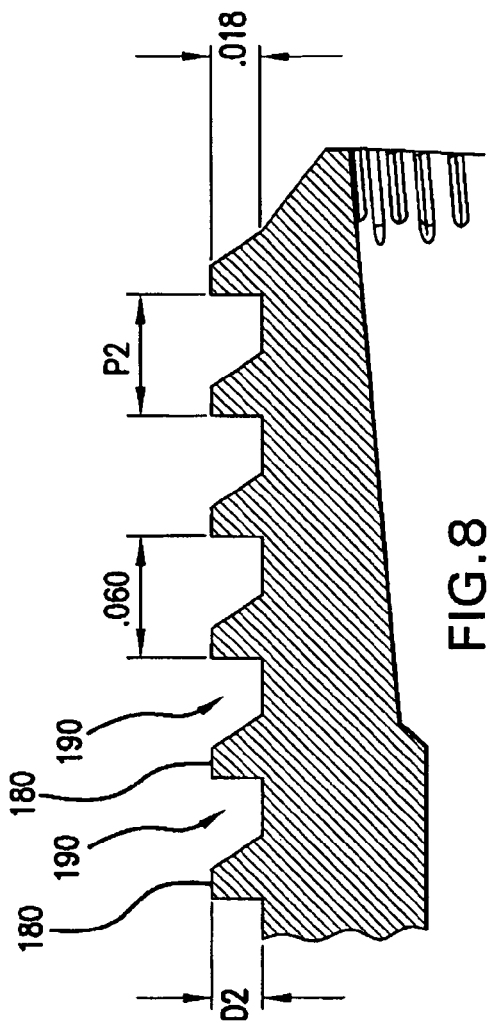
FIG. 8 is an enlarged view of a portion of an improved transverse ridge profile of a ligating dispenser device according to the invention.
Figure 9:
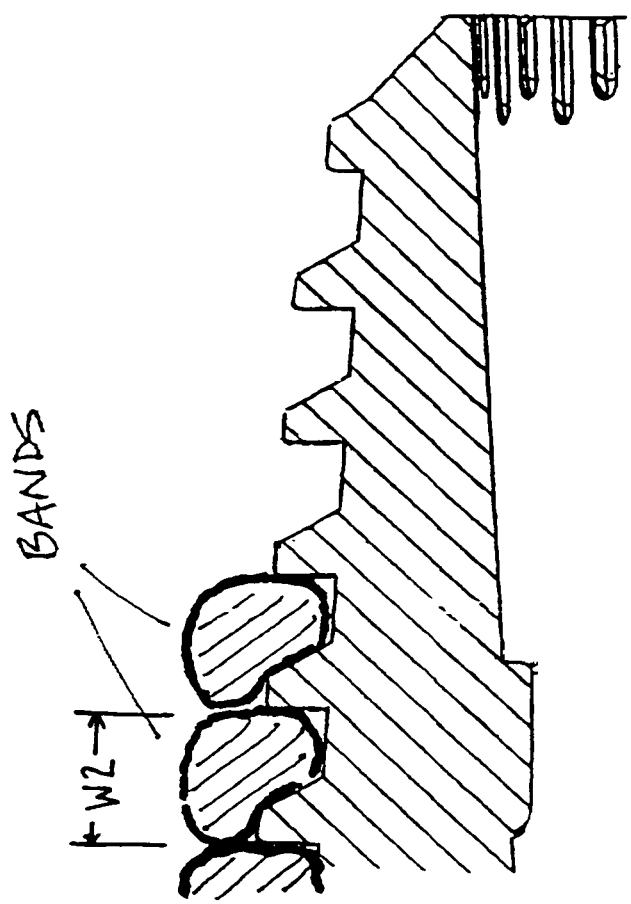
FIG. 9 shows the portion of the transverse ridge profile of the ligating dispenser device of FIG. 8, with ligating bands in place.

The present invention is directed to an improved distal end for a ligating band dispenser, wherein the device has a transverse groove or ridge profile that promotes rolling of the bands. One example of an embodiment according to the present invention is illustrated in FIG. 8. As shown in FIG. 8, the device has a groove pitch P2 of approximately 0.060" and groove depth D2 of approximately 0.018". The ligating bands for use with this embodiment of the device according to the invention are shown stretched on the housing in FIG. 9. These ligating bands have a relaxed (off housing) outer diameter (OD) of 0.245", a relaxed inner diameter (ID) of 0.075", a relaxed wall height (i.e., the distance between the ID and OD) of 0.085", and a relaxed width (measured in the direction along an axis passing through the center of the band) of 0.085". Because the width is substantially the same as the wall height, the cross-section geometry of these bands is substantially square. When stretched onto the housing as shown in FIG. 9, the width W2 of the bands is reduced to approximately 0.060". Since the groove pitch is also approximately 0.060", the width of the bands in this embodiment when stretched on the support surface is substantially the same as the pitch of the transverse grooves or ridges on the support surface. Having the width of the bands when stretched on the support surface be substantially the same as the pitch of the transverse grooves or ridges on the support surface allows the bands to fit within the grooves, as shown in FIG. 9. As will be appreciated by persons of ordinary skill in the art, this configuration helps insure that the bands are sufficiently held back by the ridge crests to induce a rolling action when the trigger line pulls on the bands.

In another embodiment of the invention, the ligating bands and the transverse grooves or ridges on the support surface may be dimensioned such that the width of the bands when stretched on the support surface is less than the pitch of the transverse grooves or ridges on the support surface. Having the width of the bands when stretched on the support surface be less than the pitch of the transverse grooves or ridges on the support surface also allows the bands to fit within the grooves, which again helps insure that the bands are sufficiently held back by the ridge crests to induce a rolling action.

In another aspect of the invention, in addition to having the pitch of the transverse grooves or ridges be substantially the same as or greater than the width of the stretched bands, the transverse grooves or ridges may also be dimensioned such that the height of the ridge crests is sufficiently high to insure that the bands are sufficiently held back by the ridge crests to induce a rolling action. Thus, for example, the groove depth D2, which also corresponds to the height of the ridge crests, may be approximately 0.018", as shown in FIG. 8.

The transverse groove or ridge profile as described herein may be used on any suitable ligating band dispensing device, for example a ligating band dispensing device similar to that shown or described in the Fortier '865 patent or as described or depicted herein. Persons of ordinary skill in the art will appreciate that modifications may be made to the above-described embodiments without departing from the scope of the invention. For example, other dimensions may be chosen for the ligating bands or the groove or ridge pitch or height, so long as the principles described herein are still followed. The full scope of protection sought for the invention is defined in the appended claims.

What is claimed is:

1. A ligating band dispensing device comprising:
   (a) a supporting structure comprising a substantially cylindrical support surface adapted to receive a plurality of ligating bands and a trigger line on an outer surface thereof, wherein the support surface has a proximal end and a distal end and a channel extending axially therethrough from the distal end to the proximal end, wherein the support surface includes at least one primary ridge maintaining the plurality of ligating bands in a position remote from the trigger line, and wherein the at least one primary ridge includes a plurality of transverse ridges on an outer face; and
   (b) a plurality of ligating bands stretched onto the support surface and adapted to be deployed off of the distal end of the support surface;
   wherein the ligating bands and the transverse ridges on the support surface are dimensioned to induce a rolling action, the width of the bands when stretched on the support surface being substantially the same as the pitch of the transverse ridges on the support surface and each band abutting against the transverse ridge that is adjacent to the band on the distal side of the band.

2. The ligating band dispensing device according to claim 1, wherein the width of the bands when stretched on the support surface is approximately 0.060 inches.

3. The ligating band dispenser device according to claim 2, wherein the height of the transverse ridges is approximately 0.018 inches.

4. The ligating band dispensing device according to claim 2, wherein the pitch of the transverse ridges on the support surface is approximately 0.060 inches.

5. The ligating band dispensing device according to claim 1, wherein the support surface has an outer diameter of approximately 0.4 to 0.6 inches.

6. The ligating band dispensing device according to claim 1, wherein the support surface further includes a plurality of slots disposed on the distal end for retaining the trigger line, and wherein the support surface includes a total number of the slots so that, when the ligating bands and the trigger line are arranged on the support surface, the trigger line passes through each slot at most once.

7. The ligating band dispensing device according to claim 1, comprising a plurality of shallow slots and deeper slots, wherein the plurality of shallow slots and deeper slots are grouped in slot pairs, each of the slot pairs including one of the shallow slots and an adjacent one of the deeper slots, and wherein each of the slot pairs is disposed between a corresponding pair of the primary ridges.

8. The ligating band dispensing device according to claim 1, the outer surface of the support surface further including at least one axially extending secondary ridge, the at least one secondary ridge maintaining the ligating bands remote from the support surface.

9. A method of deploying ligating bands comprising:
   providing a supporting structure comprising a substantially cylindrical support surface adapted to receive a plurality of ligating bands and a trigger line on an outer surface thereof, the support surface having a proximal end and a distal end and a channel extending axially therethrough from the distal end to the proximal end, the support surface including at least one axially extending primary ridge disposed on the outer surface, said at least one primary ridge maintaining the plurality of ligating bands in a position remote from the trigger line, wherein said at least one primary ridge includes a plurality of transverse ridges on an outer face;
   providing a plurality of ligating bands stretched onto the support surface and adapted to be deployed off of the distal end of the support surface, wherein the ligating bands and the transverse ridges on the support surface are dimensioned such that the width of the bands when stretched on the support surface is substantially the same as the pitch of the transverse ridges on the support surface so that the ligating bands fit between the transverse ridges with each band abutting against the transverse ridge that is adjacent to the band on the distal side of the band; and
   actuating the trigger line so as to induce a rolling action in said ligating bands toward the distal end of the supporting structure.

10. The method of deploying ligating bands according to claim 9, wherein the height of the transverse ridges is dimensioned to insure that the ligating bands are sufficiently held back by the transverse ridges to induce a rolling action.

11. The method of deploying ligating bands according to claim 9, wherein each ligating band is positioned adjacent a corresponding transverse ridge with the corresponding transverse ridge positioned between the corresponding ligating band and the distal end of said support surface, and wherein the plurality of ligating bands are arranged on the support surface such that only one transverse ridge is located between two adjacent ligating bands.

* * * * *